United States Patent [19]
Jarrell et al.

[11] Patent Number: 5,436,446
[45] Date of Patent: Jul. 25, 1995

[54] ANALYZING TIME MODULATED ELECTROSPRAY

[75] Inventors: Joseph A. Jarrell, Newton Highlands, Mass.; Michael J. Tomany, Thompson, Conn.

[73] Assignee: Waters Investments Limited, Wilmington, Del.

[21] Appl. No.: 199,406

[22] Filed: Feb. 22, 1994

Related U.S. Application Data

[63] Continuation-in-part of Ser. No. 866,605, Apr. 10, 1992, Pat. No. 5,306,910.

[51] Int. Cl.$^6$ .............................................. H01J 49/10
[52] U.S. Cl. ...................................... 250/288; 250/286
[58] Field of Search .................... 250/288, 288 A, 286

[56] References Cited

U.S. PATENT DOCUMENTS

| | | | |
|---|---|---|---|
| 4,542,293 | 9/1985 | Fenn et al. | 250/288 |
| 4,968,888 | 11/1990 | Appelhans et al. | 250/288 |
| 5,070,240 | 12/1991 | Lee et al. | 250/288 |
| 5,171,990 | 12/1992 | Mylchreest et al. | 250/288 |
| 5,306,410 | 4/1994 | Jarrell et al. | 250/286 |

Primary Examiner—Jack I. Berman
Attorney, Agent, or Firm—Huw R. Jones; Paul J. Cook; Andrew T. Karnakis

[57] ABSTRACT

A system for forming a time modulated electrospray from a sample solution is provided. Further systems for analyzing this time modulated electrospray also are provided. An element connected to a time modulated voltage source is positioned substantially opposite an electrospray apparatus and an analytical apparatus so that the initial direction of travel of the electrospray is reversed and the electrospray is diverted into the analytical apparatus. A second time modulated voltage can be provided which causes the periodic deflection of an ion beam, resulting from a time modulated electrospray, into a mass analyzer in a vacuum system. The modulation of this second voltage source is coordinated with the time modulation of the first voltage source which causes the formation of an electrospray in such a manner that efficiency of sample introduction into the mass analyzer is improved.

10 Claims, 3 Drawing Sheets

ANALYZING TIME MODULATED ELECTROSPRAY

The application is a continuation in part of application Ser. No. 866,605, filed Apr. 10, 1992, now U.S. Pat. No. 5,306,910.

BACKGROUND OF THE INVENTION

This invention relates to the generation of a time-modulated electrospray. Electrosprays are useful for analyzing solutes in a sample solution. More particularly the present invention provides a method and apparatus for intermittently forming an electrospray from a sample solution which is subsequently analyzed.

A liquid flowing through a capillary jet or orifice may be converted to a spray of small charged droplets (of the order of 1 μm in diameter) by applying a strong electric field to the liquid as it emerges from the tip of the capillary. For sufficiently high applied field, the electrostatic stress imposed by the field and the surface-induced electrical charge is sufficient to overcome the surface tension forces on the liquid. Breaking apart into a large number of small charged droplets is a way for the liquid to disperse the charge and reach a lower total energy state. This process of forming a spray is commonly known as electrospray.

Previous applications of the electrospray process to mass spectrometry regard electrospray as a steady-state process. The applied electric field referred to above is kept constant in time and, as a result, spray formation is constant in time. In a recent abstract on coupling electrospray to a time-of-flight mass spectrometer, Whitehouse, et al state that electrospray is an inherently DC phenomenon, requiring the continuous presence of a strong potential gradient about a sharp needle tip to form charged droplets, "Electrospray ionization on an ion storage time-of-flight mass spectrometer" J. G. Boyle et al, extended abstracts from the 12th International Mass Spectrometry Conference, Aug. 26–30, 1991 in Amsterdam, Holland, abstract #WeM-DO4 on p. 238.

At the present time apparatus are available for forming an electrospray of a sample solution such as a liquid stream effluent from a liquid chromatography separation step and subsequently analyzing the electrospray with a mass analyzer such as a quadrupole mass spectrometer, an ion trap, a time-of-flight mass spectrometer or a magnetic sector mass spectrometer or the like. In any kind of mass spectrometer (MS) manipulation of analysis that requires a finite time to accomplish or in which ions need to be stored whether prior to or as part of the analysis, such as in a time-of-flight mass spectrometer, a quadrupole ion trap, many implementations of MS/MS, or a Fourier Transform mass spectrometer, a non-continuous source of the electrospray can provide increased efficiency of analysis. Thus, for example in the case of an ion trap, ions are accumulated and stored in a small volume by appropriate electric fields. The mass-to-charge spectrum of these accumulated ions cannot be ascertained until the trap is "swept clean", i.e., voltages are applied to the trap that sequentially cause ions to be ejected and detected. It is only by virtue of the parameters that cause their ejection that their mass-to-charge ratio is known. During this readout interval, newly formed electrospray ions cannot efficiently be introduced into the trap, thus, they are wasted. Similarly, a the-of-flight mass spectrometer analyzes ions of different mass-to-charge ratio, by releasing or creating a burst of ions of a given energy, and then measuring the differences in their mass-to-charge ratio on the basis of their differing transit times along some predetermined trajectory. Newly created ions cannot be introduced during this transit period without potentially confusing the analysis. Thus, new ions generated during this transit time are wasted.

In most prior electrospray sources, the electrospray capillary must be maintained at a high electrical potential with respect to ground if the mass-to-charge analyzer and its vacuum housing are to be kept close to ground potential. This means that any means to introduce liquid to the electrospray source such as a liquid chromatograph or pump, must either also be maintained at a high electrical potential with respect to ground, or must be connected to the electrospray capillary by long lengths of narrow bore insulating tubing. This can compromise system performance as well as present something of a safety hazard.

In a liquid chromatograph, a stream of solvent, containing a mixture of chemical species in solution, is passed at elevated pressure through a chromatographic column. The column is so designed that it separates the mixture, by differential retention on the column, into its component species. The different species then emerge from the column as distinct bands in the solvent stream, separated in time. The liquid chromatograph provides therefore, an ideal device for the introduction into a mass spectrometer of single species, separated from initially complex mixtures.

It has been proposed in U.S. Pat. No. 4,545,293 to use a strong gas flow to entrain ions and droplets through a capillary composed of an insulator such that they migrate against the opposing electric field across that capillary, i.e., the viscous drag of the gas flow on these ions or droplets present is larger than the electrostatic force on the ions. A specific benefit of this arrangement is that it can allow the capillary, from which the electrospray emanates, and the mass analyzer to be maintained at relatively arbitrary electrical potentials, or most conveniently, they may be both at ground. In this system, however, charged droplets and ions may deposit on the inner wall of this insulated capillary. This charge then may leak away at an indeterminate rate which may affect interface stability.

Accordingly, it would be desirable to provide a method and apparatus for modulating the conversion of a liquid sample into a form such as an electrospray which permits subsequent analysis in a mass spectrometer or the like. In addition, it would be desirable to provide such an apparatus wherein the liquid sample can be converted to an electrospray and both apparatus for producing the electrospray and the electrospray analysis apparatus can be maintained at close to ground electrical potential. Such a method and apparatus would minimize sample waste and would provide a safe and efficient means for analyzing the sample.

SUMMARY OF THE INVENTION

The present invention provides a method and apparatus for forming a time modulated electrospray from a solution containing a solute sample. A solution containing the sample is passed through a capillary and emerges from an exit end of the capillary where it is converted to a time modulated electrospray by the application of a time modulated electric field. An element to which is applied a time modulated voltage is positioned substantially opposite the electrospray means and the analyzer. This element is positioned to effect a reversal of the initial direction of flow of the electrospray and to direct the reversed electrospray into the analyzer. This arrangement has the advantage that sufficiently large droplets, weakly charged droplets, or uncharged droplets will not reverse directions and enter the analyzer. Since these droplets do not contribute significantly to the ultimate signal, but do tend to contaminate the interface, and can also contribute to background noise, this arrangement requires less interface maintenance and can provide better sensitivity. The analyzer is capable of analyzing the mass to charge spectrum of the sample solute. By utilizing a time modulated electrospray the flow of sample can be modulated to accommodate the capacity of the analyzer to analyze ionized sample on an intermittent basis. Thus, the sample can be more efficiently analyzed.

The electrical potential of the electrospray means can be maintained at ground, or close to ground, electrical potential since the electrical field driving force to effect electrospray flow between the capillary and the analyzer is provided by the intermediate time modulated voltage applied to this intermediate element.

Any of the methods and apparatus for analyzing a time modulated electrospray described above may also be used in conjunction with means, such as a pulsed valve, that permit the modulation of flow into the analyzer vacuum system. In conventional schemes, ambient gas is introduced continuously into the analyzer vacuum system along with the electrospray. When utilizing the time modulated electrospray, the entrance to the analyzer vacuum system can be opened and closed in such a manner that the intervals during which it is open coincide with the arrival of the pulses of electrospray. This permits a reduction in the vacuum pumping capacity of the system, since ambient gas is only introduced into the vacuum system when electrospray is present.

BRIEF DESCRIPTION OF THE DRAWINGS

FIG. 1b illustrates a typical voltage applied to element 60 of FIG. 1a.

For the sake of clarity, only connections of time modulated voltages are shown in these figures.

DESCRIPTION OF SPECIFIC EMBODIMENTS

Figure 1A:
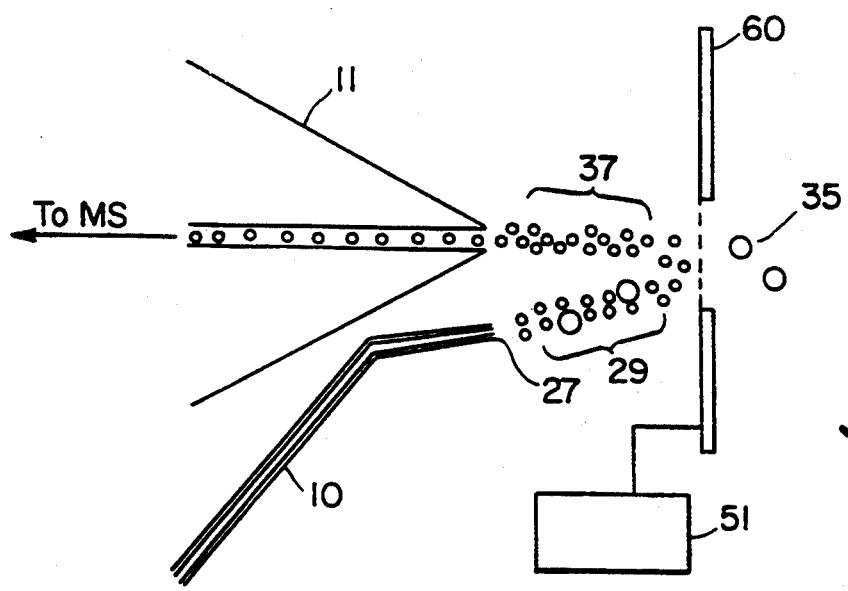
FIG. 1a illustrates a basic form of the invention in which a time modulated voltage is applied to an element positioned so as to form a time modulated electrospray and then reverse the direction of travel of the electrospray.

The method and apparatus for analyzing a time modulated electrospray comprise an electrospray means and the analyzer in which both are positioned opposite an element. The most general form of the present invention may be understood by reference to FIGS. 1a, 1b and 1c. FIG. 1a depicts a passageway 10, an element 60 and an entrance to an analytical device 11. In conventional electrospray, a constant electrical field is imposed on the tip region 27 of the passageway 10 by applying a constant electrical potential difference between passageway 10 and element 11. In addition, the tip region 27 is positioned opposite the device 11 so that the electrospray is directed into the element 11 and element 60 is not present.

In contrast, in this invention, the constant electrical potential difference is replaced by a time modulated electrical potential difference, such as can be applied by a time modulated voltage supply 51, such that a time modulated electrospray is generated by a suitable choice of potentials. The initially produced electrospray 29 is directed toward element 60 which effects a reversal of electrospray direction so that the reversed electrospray 37 is directed into analytical device 11. Large, uncharged or poorly charged droplets 35 can substantially pass through apertures in element 60 and do not contact device 11.

Figure 1B:
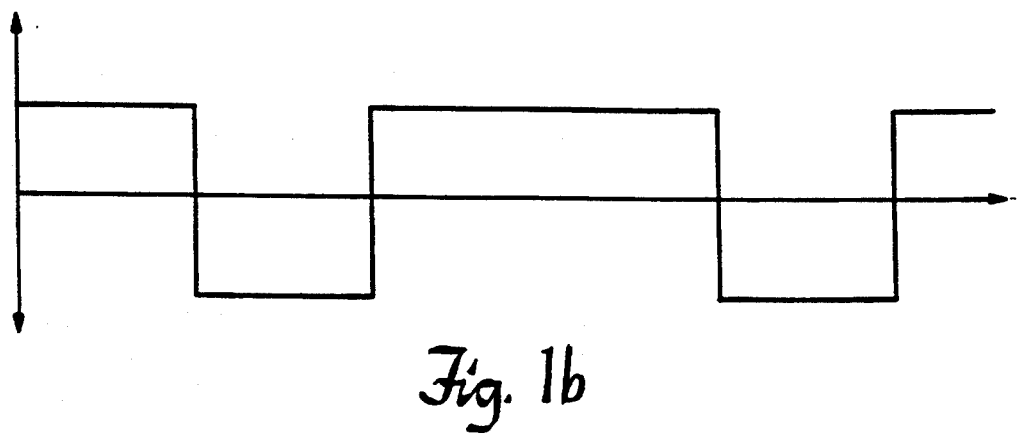
Figure 1C:
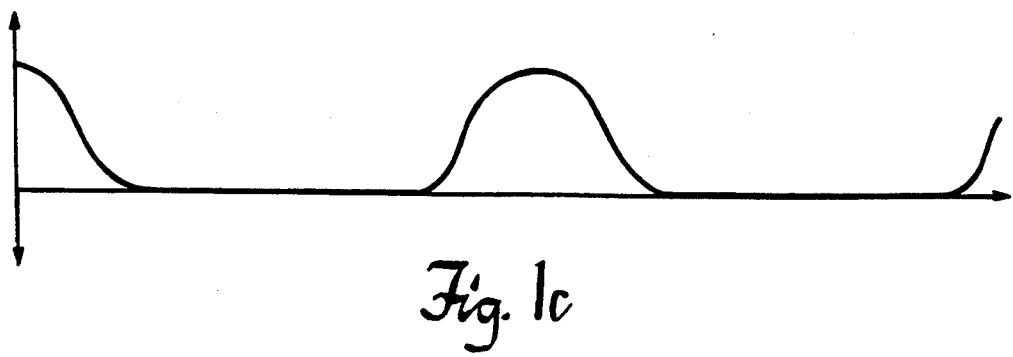
FIG. 1c illustrates an ion signal recorded by a mass-to-charge analyzer when set to record one charge state of a sample ionized according to the invention.

The following more detailed descriptions describes typical electrical potentials used to form positive electrosprayed ions, but the process is the same for negative ion formation except that the polarity of the applied potentials typically needs to be reversed. The magnitude of values mentioned or shown is less important than the relative values of the different potentials. Referring to FIGS. 1a, 1b and 1c, a passageway 10 may be kept at ground or near ground potential at all times. Likewise the entrance to an analytical device, which may typically be a housing 11, may also be kept at ground or more typically at a few hundred volts positive with respect to ground at all times. An element 60 is placed roughly opposite the exit of passageway 10 and housing 11 as shown in FIG. 1a. The electrical potential applied to element 60 is modulated as shown schematically in FIG. 1a. First a negative potential is applied (typically 1-6 Kilovolts) to element 60. This imposes a field on the fluid emerging from the exit end 27 of passageway 10 that induces positive charge on that fluid resulting in an electrospray of positively charged droplets. These droplets then migrate towards element 60. If this negative potential on element 60 were maintained, droplets and any ions present would ultimately come to rest on element 60

After a short duration of time, however, (typically between 10 and 5000 microseconds), the polarity of the electrical potential imposed on element 60 is reversed to a value of a similar magnitude, such that any ions and charged droplets present are now driven back towards housing 11 by the field between housing 11 and element 60. A specific advantage of this configuration is that uncharged or weakly charged droplets will not reverse their direction of travel. If element 60 is a solid plate they will impinge on it. Alternately, if element 60 comprises an aperture or is a grid, these uncharged or weakly charged droplets will pass through it. Since such droplets typically do not contribute usefully to the desired signal and can only contaminate the interface, it is beneficial to be able to discriminate against them by this means. By suitable adjustment of the amplitudes and durations of the negative and positive applied voltages, it is possible to alternatively form positively and negatively charged sprays. Suitable modulation of the voltages on the remaining interface elements and on the mass spectrometer will allow the alternate detection of positive and negative ions. Additionally, with suitably fast modulation, positively and negatively charged sprays could overlap such that it may be possible to reduce the net space charge of the charged stream. This would allow for a tighter focusing of the charged stream enabling a more efficient introduction of the charged stream through the rest of the interface and into the mass spectrometer.

It will also be recognized that the element 60 could be shaped so as to assist in focusing the reversed electrospray 37 onto the entrance element 11. Furthermore element 60 could consist of several sub-elements each of which could be set at somewhat different electrical potentials to provide a focusing and aligning effect.

In a particular form, when the element 11 provides a means of entry into an analytic device such as an ion trap or a time-of-flight mass spectrometer, sample in solution is not converted to an electrospray until the analytic device is ready to accept it. This enables more efficient analysis of sample. In addition by using a bipolar modulating electrical potential, both positively and negatively charged sprays can be generated essentially simultaneously. This is useful because some samples in solution are more efficiently analyzed frown positively charged electrosprays, whereas other samples in solution are more efficiently analyzed from negatively charged electrosprays. This is particularly useful when a sample introduction means such as a liquid chromatograph is interfaced to a mass analyzer since it reduces by roughly two-fold, the time required for an analysis by both positive and negative electrospray. In conventional electrospray means, two repetitive liquid chromatographic separations would be required. With a time modulated electrospray, analysis of both positive and negative electrospray can be effected in one ran. Since a typical prior art chromatographic separation of a complex mixture of biomolecules can easily take an hour, the present invention provides a significant time savings.

In a preferred form of this invention, the passageway 10 is formed from an electrically insulating material such as glass, quartz, synthetic polymeric composition or the like.

This use of time modulated electric fields to reverse the direction of charged particles formed by an electrospray may be also usefully employed to likewise reverse the direction of charged particles formed by other electrified sprays.

More generally, while the above descriptions of these techniques are based on the charged particles in question being in a gaseous medium, these techniques also may usefully be employed in other fluid mediums.

It is possible to add additional grids and modulating voltages to the same effect, in essence forming a peristaltic pump for charged particles. These techniques can also be used with grids that are not perfectly parallel i.e. to cause charged particles to turn corners.

Time modulated electric fields also can be usefully employed to likewise change the energy state of electrically charged particles that are generated by other techniques well known in the art. Examples of such techniques are nebulization techniques that employ thermal, pneumatic, or ultrasonic means, or various combinations thereof. Some of these examples are frequently referred to by their trade names as Ionspray and Thermospray. As used herein the term electrified spray or electrospray is used to mean either an electrospray or an electrified spray in which nebulization is assisted by any, or any combination of, thermal, pneumatic, or ultrasonic means.

More generally, while the above descriptions of these techniques are based on the charged particles in question being in a gaseous medium, these techniques also can be usefully employed in other fluid mediums.

While this invention might most typically be used as described above, to permit both the electrospray capillary and the mass-to-charge analyzer and its vacuum housing to be kept close to ground, the same principles can be used to raise the electrical potential at which droplet or ions find themselves so as to facilitate their optimal introduction into a magnetic sector mass spectrometer. Similarly, other voltage time profiles are applicable. In the examples described here, the modulating voltages make discrete level shifts in time, i.e. they are depicted by rectangularly shaped pulses. This invention can also be implemented, for example, with sinusoidal voltage time variations or many other periodic or roughly periodic variations of voltage in time.

A further improved method and apparatus for analyzing a time modulated electrified spray comprises a second time modulated voltage which causes the periodic deflection of an ion beam into a mass analyzer in a vacuum system. The modulation of this second voltage source is coordinated with the time modulation of the first voltage source, which causes the formation of an electrospray or electrified spray in such a manner that efficiency of sample introduction into the mass analyzer is improved. Typical systems where this invention and usefully applied include the reflecting time-of-flight mass spectrometer described by Dodonov et al in Soviet Union Patent SU 1681430 A1 and in "Atmospheric pressure ionization time-of-flight mass spectrometer" A. F. Dodonov et al, extended abstracts from the 12th International Mass Spectrometry Conference, Aug. 26–30, 1991 in Amsterdam, Holland, abstract #TuA-D20 on p. 153 or the system described by Lee et al in U.S. Pat. No.5,070,240. It will be recognized that it is equally useful to coordinate any time modulated electrospray with a time modulated voltage which causes the periodic deflection of an ion beam into a mass analyzer in a vacuum system. Other such time modulated electrosprays are described in copending application Ser. No. 866,605, filed Apr. 10, 1992, now U.S. Pat. No. 5,306,910.

A further improved method and apparatus for analyzing a time modulated electrified spray comprises an electrified spray means and the analyzer and an entry valve to the analyzer. The characteristics of the valve are such that it may be rapidly opened and closed so that the intervals during which it is open coincide with the arrivals of the pulses of electrified spray or ion stream. This permits a reduction in the vacuum pumping capacity of the system, since ambient gas is only introduced into the vacuum system when a useful signal is present. This valve may be placed at various positions in the path into the analyzer vacuum chamber. It is equally useful to coordinate any time modulated electrospray, whether or not its direction of travel has been reversed, with an entry valve whose characteristics are such that it can be rapidly opened and closed so that the intervals during which it is open coincide with the arrivals of the pulses of electrified spray or ion stream.

In general, the time modulated electric fields described above are modulated in a periodic fashion, that is at constant frequency. Clearly in an age of inexpensive microprocessors, it is possible to generate time modulated electrical fields that are not truly periodic. A Fourier analysis of such time varying fields, would nevertheless reveal strong components at the dominant frequencies. Thus in discussing the periodicity of these modulated electrical fields, it is appropriate to refer to a rough frequency. This term rough frequency is taken to mean that a Fourier analysis of the electrical field variation performed on, for example a 10 second interval of the time modulated electrical field would have a major frequency amplitude at that frequency.

Several specific embodiments detailing complete electrospray, interface, and mass analysis systems are described below with reference to FIGS. 2 and 3. These systems provide for the generation of electrosprays from sample solutions, and desolvation of these electrosprays to form intact ion streams consisting of ions, vapor and gas for analysis. In the following, all processes described are based on the electrical potentials which would be applied for the formation of positively charged droplets, ions and clusters. It will be evident that by suitable reversals of potentials, negatively charged droplets, ions and clusters can also be formed.

Figure 2:
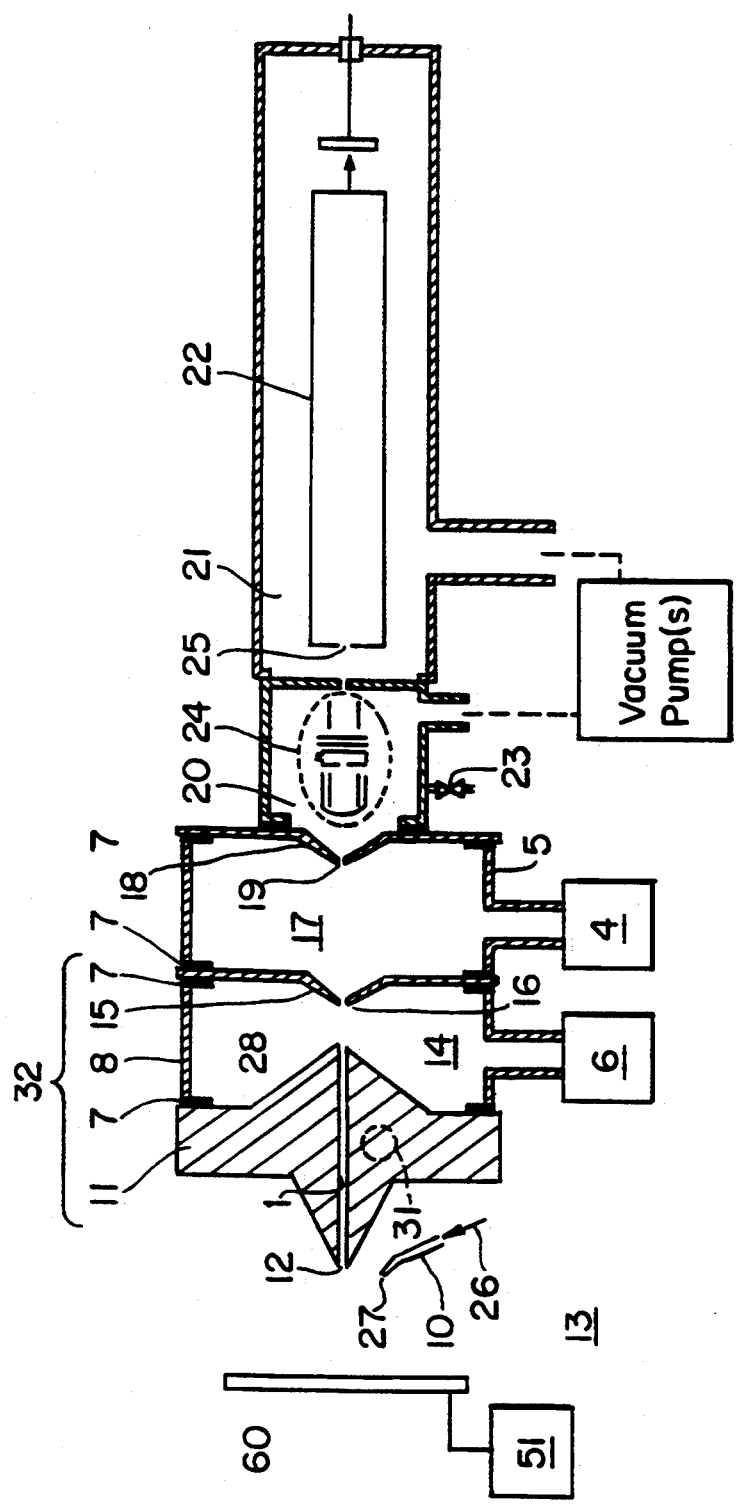
FIG. 2 is a schematic view of a preferred apparatus of this invention.

Referring to FIG. 2, the liquid to be electrosprayed (typically carrying analyte molecules of interest such as from a liquid chromatography) flows, in the direction shown by the arrow 26, into one end of the passageway 10 which may be kept at or near electrical ground potential at all times. As it emerges from the exit end 27 of this capillary, the liquid is converted to a time modulated electrospray, as described above, by virtue of the time modulated electrical potential difference between the exit end 27 at the tip of passageway 10 and element 60 which is connected to time modulated voltage supply 51. This end 27, from which the liquid is electrosprayed is positioned between a housing 11 and element 60 such that the electrospray emerging from tip 27 initially travels away from housing 11. The element 60 is positioned roughly opposite housing 11, which is heated and is electrically conductive. As described above, element 60 serves to reverse the direction of travel of the time modulated electrospray so that it can enter orifice 12 in housing 11.

Housing 11 forms a wall of chamber 32, which consists of housing 11, wall portion 8, skimmer 15 and two insulating portions 7. Housing 11 is electrically insulated by an insulating portion 7 from its surrounds and thus may be set at an arbitrary electrical potential with respect to ground. Housing 11 is traversed by a passageway 1 and includes a heater 31 such as an electrical cartridge heater. Passageway 1 has an entrance orifice 12 and an exit orifice 28. The entrance orifice 12 of passageway 1 is positioned at the apex of housing 11. Typically, the length of the passageway 1 is between about 1 and 4 cm. The housing 11 is formed of an electrically and thermally conductive material such as aluminum which is heated to a temperature between about 65_C and 220_C, preferably between about 100_C and 130_C. The housing 11 can be formed of a metal such as aluminum or stainless steel. The housing 11 can be heated by any conventional means such as by electrical resistance heaters 31 imbedded in the housing or by internal conduits for heated heat exchange fluid. In any event, uniform heating of the passageway can be easily effected due to its mass and material of construction. The passageway 1 through housing 11 may be contoured in such a way as to optimize thermal transfer from the housing 11 to the ion stream. The housing 11 also serves as a wall between a region of atmospheric pressure 13 and a region of lower pressure 14. Region 14, is maintained at this lower pressure, typically 4–20 Torr by the action of a small rotary pump 6. The housing 11 is typically maintained at a temperature of from 100–220_C. The pressure drop across it causes the ambient atmosphere in region 13 to be dram into the orifice 12. This gas flow, in conjunction with the electric fields between the grid 60 and the housing 11, causes some of the electrosprayed droplets, ions, clusters and vapors to enter orifice 12 and enter passageway 1. As these droplets pass through the passageway 1, heat is transferred to them thus promoting desolvation and some ion evaporation. The housing 11 has sufficient mass, typically greater than about 50 g, to effect this heat transfer. The housing 11 used in conjunction with the grid 60 having a time modulated voltage applied to it, constitutes a preferred embodiment of this invention.

Region 14 is bounded by housing 11, skimmer 15 and wall portion 8. In a preferred embodiment, they are all electrically isolated from each other, by insulating portions 7, such that the shape of wall portion 8, and the electrical potential applied to it, can be used to optimize charged particle transmission. It is, however, also possible for wall portion 8 to be electrically part and/or mechanically part of either housing 11 or skimmer 15. The distance between the exit orifice 28 of passageway 1 and the orifice 16 of skimmer 15 is typically between about 0.1 and 0.5 cm.

The ion stream of air, droplets, ions, gas, clusters, and vapor emerges from orifice 28 into region 14 and impinges on a conductive skimmer 15 that is electrically insulated from its surrounds and thus may be set at an arbitrary electrical potential with respect to ground. Typically it operates at a potential such that there exists an electrical field between housing 11 and skimmer 15 that tends to focus charged particles towards skimmer 15. Because collisions between charged ion stream components (e.g. ions, charged droplets, charged clusters and solvated ions) and neutral gas and vapor molecules occur in this region 14 as the ion stream traverses region 14 on their way to skimmer 15, additional desolvation, ion evaporation and declustering occur. The energy of these collisions can be affected by the potential difference between the housing 11 and skimmer 15. A portion of the ion stream arriving at skimmer 15 traverses the orifice 16 at its apex and enters region 17 and impinge on a conductive skimmer 18 that is electrically insulated from its surrounds and thus may be set at an arbitrary electrical potential with respect to ground. Region 17 is maintained at a lower pressure, typically 0.1–3 Torr by another rotary pump 4. Again, because collisions between charged ion stream components, e.g. charged droplets, charged clusters and solvated ions, and neutral gas and vapor molecules occur in this region 17 as the ion stream traverses it on its way to skimmer 18, additional desolvation and ion evaporation occurs.

Because of the lower pressure in this region, the energy of these collisions is considerably affected by the potential difference between skimmer 15 and skimmer 18 such that considerable desolvation and ion evaporation may occur. The energy of collisions in this region can be controlled by the electrical potential difference between these regions. Indeed these collisions can be sufficiently energetic that fragmentation of ionized analyte molecules can occur providing useful structural information.

Region 17 is bounded by skimmer 15, skimmer 18 and wall portion 5. In a preferred embodiment, they are all electrically isolated from each other by insulating portions 7, such that the shape of wall portion 5, and the electrical potential applied to it, can be used to optimize charged particle transmission. It is however, also possible for wall portions 5 to be electrically part and/or mechanically part of either skimmer 15 or skimmer 18.

A portion of the ion stream arriving at skimmer 18 traverses an orifice 19 at the apex of skimmer 18 and enters region 20. Region 20 is typically separated from the region 21 containing a mass analyzer 22 and each region is separately pumped but this is not mandatory. In other embodiments, regions 20 and 21 may not be separated. In either case, ion optics 24 are contained in region 20 that serve to focus ions, emerging into region 20, via orifice 19, onto the entrance aperture 25 of the mass analyzer 22. Typically, this can be a quadrupole mass spectrometer, an ion trap, a time-of-flight mass spectrometer or a magnetic sector mass spectrometer.

In a preferred embodiment, however, shown in FIG. 2, these ion optics are also designed such that they can also serve to ionize neutral gas molecules, introduced into region 20 through leak valve 23, by conventional electron impact ionization. The benefit provided by this arrangement is that the mass axis of the mass analyzer may be calibrated with well-known, easily purified, low molecular weight compounds, typically perfluorotributylamine.

Figures 3, 3A:
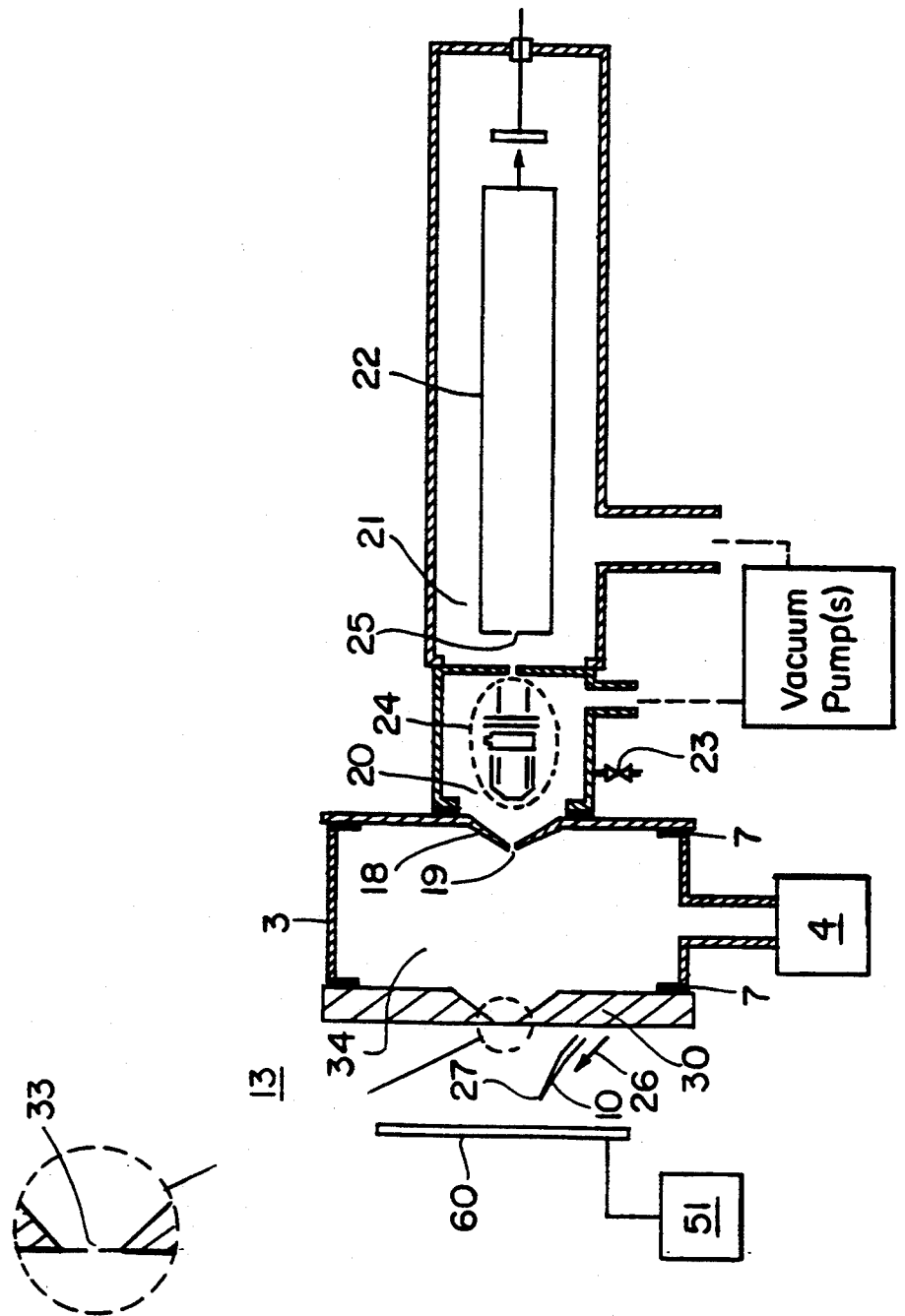
FIG. 3 is a schematic view of an alternative apparatus of this invention.
FIG. 3a is an enlarged view of the orifice portion of FIG. 3.

For the sake of simplicity, those elements of FIG. 3 that are in common with their counterparts in FIG. 2 retain the stone reference numerals.

Referring to FIG. 3, the liquid to be electrosprayed typically carrying analyte molecules of interest such as from a liquid chromatograph, flows, in the direction shown by the arrow 26, into one end of the passageway 10 which may be kept at or near electrical ground potential at all times. As it emerges from the other end of this capillary, the liquid is converted to a time modulated electrospray, as described above, by virtue of the time modulated electrical potential difference between the exit end 27 at the tip of passageway 10 and element 60 which is connected to time modulated voltage supply 51. This end 27, from which the liquid is electrosprayed, is positioned between an electrically conductive plate 30 and element 60 such that the electrospray emerging from end 27 initially travels away from housing 11. The element 60 is positioned roughly opposite plate 30 which is electrically isolated by insulating portions 7 from its surrounds and thus may be set at an arbitrary electrical potential with respect to ground. Plate 30 contains an orifice 33. Plate 30 also serves as a wall between a region of atmospheric pressure 13 and a region of lower pressure 34. Region 34 is maintained at this lower pressure, typically 0.5–3 Torr by the action of a small rotary pump 4. No heat need to applied to plate 30. Plate 30 can be maintained at room temperature. The pressure drop across plate 30 causes the ambient atmosphere in region 13 to be drawn through orifice 33. This gas flow, in conjunction with the electric field between the passageway 10 and plate 30, causes some of the electrosprayed droplets and ions to enter orifice 33.

This stream of air, droplets, ions and vapor emerges from orifice 33 into region 34 and impinges on a conductive skimmer 18 that is electrically insulated from its surrounds by insulated portions 7 and thus may be set at an arbitrary electrical potential with respect to ground. Typically, it operates at a potential such that there exists an electric field between plate 30 and skimmer 18 that tends to focus charged particles towards skimmer 18. Because of collisions of both charged ion stream components with neutral gas and vapor molecules occur in this region 34 as these droplets and solvated ions traverse it on their way to skimmer 18, considerable desolvation and ion evaporation occurs such that a usable ion signal can be produced.

Because of the low pressure in this region, the energy of these collisions is considerably affected by the potential difference between plate 30 and skimmer 18, such that considerable desolvation and ion evaporation occur. The energy of collisions in this region can be controlled by the electrical potential difference between these regions. Indeed, these collisions can be sufficiently energetic that fragmentation of ionized analyte molecules can occur providing useful structural information.

Region 34 is bounded by plate 30, skimmer 18 and wall portion 3. In a preferred embodiment, they are all electrically isolated from each other by insulating portions 7, such that the shape of wall portion 3, and the electrical potential applied to it, can be used to optimize charged particle transmission. It is, however, also possible for wall portion 3 to be electrically part and/or mechanically part of either plate 30 or skimmer 18.

Some portion of the ions and droplets arriving at skimmer 18 traverse the orifice 19 at its apex and enter region 20. Region 20 is ideally separated from the region 21 containing the mass spectrometer 22, and each region is usually separately pumped, but this is not mandatory. In other embodiments, regions 20 and 21 are not separated. In either case, ion optics 24 are contained in region 20 that serve to focus ions, emerging into region 20 (via orifice 19), onto the entrance aperture 25 of the mass analyzer 22. Typically this is a quadrupole mass spectrometer, an ion trap, a time-of-flight spectrometer or a magnetic sector mass spectrometer. In a preferred embodiment, however, shown in FIG. 3 these ion optics are also designed such that they can also serve to ionize neutral gas molecules, introduced into region 20 through leak valve 23, by conventional electron impact ionization. The benefit provided by this arrangement is that the mass axis of the mass analyzer may be calibrated with well-known, easily purified, low molecular weight compounds, typically perfluorotributylamine. Other specific benefits conferred by this design compared to previous designs are the elimination of the need for any external supply of gas, ease of disassembly and cleaning, and the ability to provide useful data with relatively modest rotary pumps. An additional feature of this scheme is that it is possible to use only one rotary pump to both evacuate region 34 and provide backing pumping for the turbomolecular or diffusion pumps needed to evacuate regions 20 and 21.

We claim:

1. Apparatus for converting a solution containing a solute sample into ionized molecules for analysis of the sample which comprises;

a passageway for passing said solution therethrough, said passageway having an exit to discharge said solution from said passageway in the form of an electrified spray and toward a means for generating a time modulated electric field, said means of generating a time modulated electric field, said time modulated electric field alternately effecting (a) the modulation of the formation of said electrified spray, and (b) a change in direction of travel of said spray toward an entry orifice of a second passageway, and said entry orifice of said second passageway positioned adjacent the exit of said first passageway such that said spray having the direction of travel reversed enters said entry orifice.

2. The apparatus of claim 1 wherein said second passageway is in communication with a mass analyzer in which analysis is based on the ratio of the mass to charge of said ionized molecules.

3. The apparatus of claim 1 wherein said second passageway is in communication with a mass analyzer in which analysis is based on the ratio of the mass to charge of said ionized molecules and wherein said solute sample comprises the effluent from a liquid chromatograph apparatus or a capillary zone electrophoresis apparatus.

4. Apparatus for converting a solution containing a solute sample into ionized molecules for analysis of the sample which comprises:
   a passageway for passing said solution therethrough, said passageway having an exit to discharge said solution from said passageway in the form of an electrified spray and toward a means for generating a time modulated electric field,
   said means of generating a time modulated electric field, said time modulated electric field effecting this modulation of the formation of said electrified spray and effecting the entry of said spray into a means for converting said electric spray into an ion beam,
   said means for converting said electrified spray into an ion beam of said ionized molecules,
   and a second means for generating a second time modulated electric field, said second time modulated electric field positioned so as to deflect said ion beam into a mass analyzer.

5. Apparatus for converting a solution containing a solute sample into ionized molecules for analysis of the sample which comprises:
   a passageway for passing said solution therethrough, said passageway having an exit to discharge said solution from said passageway in the form of an electrified spray, and toward a means for generating a time modulated electric field,
   said means of generating said time modulated electric field effecting the modulation of the formation of said electrified spray and effecting the entry of said spray into a means for converting said electric spray into an ion beam,
   means for converting said electrified spray into an ion beam of ionized molecules
   and means for time modulating entry of said ion beam into a vacuum system housing a means for analysis of said ionized molecules.

6. Apparatus for converting a solution containing a solute sample into ionized molecules for analysis of the sample which comprises;
   a passageway for passing said solution therethrough, said passageway having an exit to discharge said solution from said passageway in the form of an electrified spray and toward a means for generating a time modulated electric field,
   said means of generating, said time modulated electric field alternately effecting (a) the modulation of the formation of said electrified spray, and (b) a change in direction of travel of said spray toward a means for converting said electric spray into an ion beam,
   means for converting said electrified spray into an ion beam of said ionized molecules,
   and a second means for generating a second time modulated electric field, said second time modulated electric field positioned so as to deflect said ion beam into a mass analyzer.

7. Apparatus for converting a solution containing a solute sample into ionized molecules for analysis of the sample which comprises:
   a passageway for passing said solution therethrough, said passageway having an exit to discharge said solution from said passageway in the form of an electrified spray, and toward a means for generating a time modulated electric field,
   said means of generating said time modulated electric field alternately effecting (a) the modulation of the formation of said electrified spray, and (b) a change in direction of travel of said spray toward a means for converting said electric spray into an ion beam,
   means for converting said electrified spray into an ion beam of ionized molecules
   and means for time modulating entry of said ion beam into a vacuum system housing a means for analysis of said ionized molecules.

8. The apparatus of any one of claims 1, 2, 3, 4, 5, 6 or 7 wherein the frequency of time modulation of said electric fields is greater than about 1 Hz.

9. The apparatus of any one of claims 1, 2, 3, 4, 5, 6 or 7 wherein the frequency of time modulation of said electric fields is greater than about 200 Hz.

10. Apparatus and method for converting a solution containing a solute sample into ionized molecules for analysis of the sample which comprises
    means for converting said solution to an electrified spray,
    means for converting said electrified spray into an ion beam of said ionized molecules,
    means for reducing the space charge of said ion beam,
    and a mass analyzer in which analysis of said ion beam is based on the ratio of the mass to charge of said ionized molecules.

* * * * *